United States Patent [19]

Chen et al.

[11] Patent Number: 5,107,059

[45] Date of Patent: Apr. 21, 1992

[54] ISO/NORMAL PARAFFIN SEPARATION BY MEMBRANE EXTRACTION

[75] Inventors: Tan-Jen Chen, Clearwater, Canada; James R. Sweet, Baton Rouge, La.

[73] Assignee: Exxon Research & Engineering Company, Florham Park, N.J.

[21] Appl. No.: 622,689

[22] Filed: Dec. 5, 1990

[51] Int. Cl.$^5$ .................... C07C 7/144; B01D 11/00
[52] U.S. Cl. .................... 585/818; 208/308; 210/644; 210/650; 210/651
[58] Field of Search ............... 585/818; 210/644, 650, 210/651; 208/308

[56] References Cited

U.S. PATENT DOCUMENTS

| | | | |
|---|---|---|---|
| 2,947,687 | 8/1960 | Lee | 210/23 |
| 3,043,891 | 7/1962 | Stuckey | 260/674 |
| 3,140,256 | 7/1964 | Martin et al. | 210/23 |
| 3,244,763 | 4/1966 | Cahn | 260/677 |
| 3,725,255 | 4/1973 | Barilli et al. | 208/331 |
| 3,725,256 | 4/1973 | Lugo et al. | 208/331 |
| 3,725,257 | 4/1973 | Cavenaghi et al. | 208/331 |
| 3,956,112 | 5/1976 | Lee et al. | 210/22 |
| 4,532,347 | 7/1985 | Vaughan | 562/528 |
| 4,670,151 | 6/1987 | Bitter et al. | 210/641 |
| 4,966,707 | 10/1990 | Cussler et al. | 210/632 |

OTHER PUBLICATIONS

"Microporous Membrane Solvent Extraction", Prasad, R., et al, Separation Science & Technology, 22(2&3) 619-640, 1987.
"Dispersion-Free Solvent Extraction with Microporous Hollow-Fiber Modules", Prasad, R., et al, AIChE Journal, Feb. 1988, vol. 34, No. 2, pp. 177-188.
"Designing Hollow-Fiber Contactors", Yang, M. C., et al, AIChE Journal, Nov. 1986, vol. 32, No. 11, pp. 1910-1916.
"Liquid-Liquid Extraction with Microporous Hollow Fibers", D'Elia, N. A. et al, J. Memb. Science 29 (1986) 309-319.
"Critical Entry Pressure for Liquids in Hydrophobic Membranes", Kim, B. S., et al, J. Colloid & Interface Science, vol. 115, No. 1, Jan. 1987, pp. 1-8.
"Solvent Extraction with Microporous Hydrophilic and Composite Membranes", Prasad, R., et al, AIChE Journal, Jul. 1987, vol. 33, No. 7, 1057-1066.
"Dispersion-Free Solvent Extraction with Microporous Hollow Fiber Modules", Prasad, R., et al, AIChE Summer National Meeting, Boston 1986.
"Nondispersive Solvent Extraction Using Microporous Membranes", Prasad, R., et al, AIChE Symposium, Membrane Materials & Processes, No. 261, vol. 84, 1988 (pp. 42-53).
"Hollow Fiber Solvent Extraction of Pharmaceutical Products: A Case Study", Prasad, R., et al, J. Memb. Sci. 47, 1989, 235-259.
"Novel Uses of Microporous Membranes: A Case Study", Callahan, R. W., AIChE Symposium Series, Membrane Materials & Processes, No. 261, vol. 84, 1988, pp. 54-65.

*Primary Examiner*—Anthony McFarlane
*Assistant Examiner*—Nhat Phan
*Attorney, Agent, or Firm*—Joseph J. Allocca

[57] ABSTRACT

Non-normal, branched paraffins (isoparaffins) are separated from hydrocarbon feeds comprising mixtures of isoparaffins and normal paraffins by the procedure involving the steps of contacting the hydrocarbon feed with one face of a non-selective, microporous partition barrier membrane while simultaneously contacting the opposite face of said membrane, preferably in countercurrent flow, with a polar solvent. The isoparaffins in the feed selectively permeate across the porous partition barrier membrane in response to the polar solvent to the solvent side of the membrane whereby a permeate enriched in isoparaffins and a retentate of decreased isoparaffin content as compared to the feed are obtained.

6 Claims, No Drawings

ISO/NORMAL PARAFFIN SEPARATION BY MEMBRANE EXTRACTION

BACKGROUND OF THE INVENTION

1. Field of the Invention

The present invention is a process whereby hydrocarbon feed streams comprising mixtures of non-normal, branched paraffins (i.e., isoparaffins) and normal, unbranched, straight chain paraffins (n-paraffins) are separated into a permeate stream enriched in isoparaffins and a retentate stream enriched in n-paraffins as compared to the feed by the process of contacting the hydrocarbon feed with one face of a non-selective, microporous partition barrier membrane while simultaneously contacting the opposite face of said micro-porous partition barrier membrane with a polar solvent. Preferably the feed and polar solvent are passed countercurrently across the respective faces of the microporous partition barrier membrane. The isoparaffins in the feed selectively permeate through the micro-porous partition barrier in response to the polar solvent on the solvent side of the membrane. A permeate enriched in isoparaffins and a retentate of decreased isoparaffin (but of increased n-paraffin) content as compared to the feed is obtained.

2. Description of the Related Art

The separation of isoparaffins from n-paraffins is a very desirable processing step in hydrocarbon refining. Removal of n-paraffins from the motor gasoline pool will significantly enhance the total pool octane quality.

Because the isoparaffins and n-paraffins of substantially the same carbon number range possess boiling point in overlapping ranges, separation of isoparaffins from n-paraffins by distillation is difficult. While separation based on melting point may be possible, such a separation is very energy intensive requiring extensive refrigeration to effect the separation.

The use of selective membranes has been suggested. U.S. Pat. No. 2,947,687 and U.S. Pat. No. 3,043,891 disclose the separation of hydrocarbon mixtures by passing across the face of a non-porous membrane through which at least one component of the hydrocarbon mixture will permeate.

U.S. Pat. No. 3,043,891 teaches a process for increasing the permeation rate of saturated hydrocarbons through non-porous membranes which are capable of separating hydrocarbons according to type, and/or molecular configuration, and/or boiling point or molecular weight. The patent teaches that the permeation process is increased by contacting the membrane during the permeation process with an added hydrocarbon solvent for the membrane. This solvent may contact the membrane on the feed side, the permeate side or on both sides. Representative of such permeation accelerating solvents include aromatics and unsaturated hydrocarbons such as olefins or diolefins. The solvent is described as being a solvent for the membrane, i.e., swells the membrane.

The membranes employed are described as non-porous and include natural or synthetic rubber, gum rubber, chloroprene, neoprene, vinyl polymers such as styrene polymer, polyisobutylene, certain cellulose ethers.

The patent indicates that saturated molecules will permeate through the membrane in the following sequence of increasing selectivity: open chain highly branched hydrocarbons, <open chain with lesser degree of branching; <closed chain (e.g., cycloparaffins) and alkyl cycloparaffins, <straight chain or normal paraffins (i.e., straight chain paraffins more readily permeate). Use of the membrane solvent will substantially increase the permeation without substantially altering the selectivity U.S. Pat. No. 2,947,687 teaches the separation of hydrocarbons by type through a non-porous membrane using a membrane solvent to enhance the permeation rate. Membrane solvents include substituted hydrocarbons which are soluble in, and have solvent power for, the membrane. The hydrocarbon solvent is an organic compound containing one or more atoms of halogen, oxygen, sulfur or nitrogen. Thus, materials such as carbontetrachloride, alcohols, ketones, esters, ethers, carboxylic acids, mercaptans, sulfides (e.g., diethylsulfide etc.), nitropropane, nitrobenzene, acetonitrile, formamide, ethylene diamine, etc. may be employed in an amount ranging from 1 to 100% based on total solvent to hydrocarbon feed. The process may be operated at a pressure differential between the feed and permeate zone with the permeate being removed by vacuum. Alternately the permeate can be removed by a sweep stream such as steam, air, butane, etc.

The membrane is non-porous and includes natural or synthetic rubber, vinyl polymers, cellulose esters, cellulose ethers.

The process can use any hydrocarbon source as feed and the separation achieved is in the order: saturated hydrocarbons, <unsaturated hydrocarbons, <aromatics. Saturated hydrocarbons of approximately the same boiling range permeate in the order of increasing selectively: branched chain, <cyclic-chain, <straight chain configuration, i.e., straight chain paraffins more readily permeate through the membrane.

In an example methyl cyclohexane is separated from an equal volume mixture of methyl cyclohexane and isooctane using 5% methyl ethyl ketone as solvent. An operating pressure differential of 400 mm Hg was maintained and the temperature was 52° C. and 82° C. The methyl cyclohexane preferentially permeated through the membrane.

U.S. Pat. No. 3,956,112 teaches a membrane solvent extraction process. The membrane solvent extraction system is utilized to separate two substantially immiscible liquids and extract a solute through a solvent swollen membrane from one solvent liquid phase to the extracting solvent liquid without direct contact between the liquid phases. The membrane is substantially non-porous. Table III of U.S. Pat. No. 3,956,112 compares the invention of '112 with competing processes. One of these processes is described as direct extraction via porous partition. That process is practiced using two immiscible solvents. The driving force is the chemical potential depending on the partition coefficient of the solute in the two solvents. The process employs a porous membrane or partition wall. In that process solutes from one solvent are transferred to the extraction solvent via direct solvent-solvent contact.

U.S. Pat. No. 3,140,256 teaches a membrane separation process employing a membrane comprised of a cellulose derivative (e.g., cellulose ester or ether) modified by reaction with aldehydes, organic di isocyanate, organic monoisocyanate, organo-phosphorus chlorides and organo-sulfur chlorides. Hydrocarbon feeds can be separated into these components by type using the membrane, e.g., aromatics can be separated from unsaturated hydrocarbon (olefins or di-olefins) and/or from paraffins, or branched chain aliphatic hydrocarbons can be separated from other aliphatic hydrocarbons which have a different number of branched chains. Aromatic hydrocarbons permeate more rapidly than do the saturated (i.e., paraffinic) hydrocarbons. In an example methyl cyclohexane permeated through the membrane more selectively than did isooctane.

"Microporous Membrane Solvent Extraction," Prasad, R., et al., Separation Science and Technology 22 (2&3) 619–640, 1987 examines the phenomenon of dispersion-free solvent extraction through immobilized aqueous-organic interface in a microporous hydrophobic membrane. Expressly investigated was the use of an organic-organic interface to extract aromatics as exemplified by toluene, from a hydrocarbon feedstock, as exemplified by a mixture of toluene in n-heptane, employing a microporous Celgard 2400 polypropylene membrane to partition the feed from the polar extraction solvent, which in this case was NMP. The toluene selectively permeated through the porous Celgard membrane into the NMP thereby reducing the amount of toluene in the feed (raffinate) while increasing the amount of toluene in the permeate phase (extract).

DESCRIPTION OF THE PREFERRED EMBODIMENTS

Hydrocarbon feed mixtures of n-paraffins and isoparaffins are separated into an isoparaffin rich stream and an n-paraffin rich stream by a process comprising contacting the hydrocarbon feed mixture with one side of a non-selective, microporous, partition barrier membrane while simultaneously contacting the other face of said membrane with a polar solvent whereby the isoparaffins selectively permeate through the barrier membrane in response to the polar solvent on the permeate side of the barrier membrane thereby resulting in an isoparaffins rich permeate and a retentate of decreased isoparaffins content.

Hydrocarbon feeds substantially comprising mixtures of isoparaffins and n-paraffins are separated into an isoparaffin rich stream and an n-paraffins rich stream by a process comprising contacting the hydrocarbon feed mixture with one side of a non-selective, microporous partition barrier membrane while simultaneously contacting the opposite face of said microporous partition barrier membrane with a polar solvent, the feed and polar solvent preferably passing countercurrently across the respective faces of the microporous partition barrier membrane whereby the iso-paraffins selective permeate through the barrier membrane in response to the polar solvent on the solvent side of the barrier membrane resulting in an isoparaffins rich permeate and a retentate of decreased isoparaffins (but of increased n-paraffins) content as compared to the feed.

The feed to the membrane separation process of the present invention is described as a hydrocarbon feed stream, substantially comprising a mixture of isoparaffins and n-paraffins, ranging from $C_4$ hydrocarbons to liquids with final boiling points of about 1050° F. Separation of iso from normal paraffins from such streams would have many advantages.

Alkylation efficiency is greatly enhanced as normal butane is removed from cat cracking and steam cracking $C_4$ streams. The octane quality of mogas (65°–430° F.) is greatly increased as normal paraffins are removed. The pour point and cloud point properties of lubes, including those made from Fischer-Tropsch hydroisomerized wax (600°–1050° F.) are improved as normal paraffins are removed.

The feed stream is passed along one side of a porous, non-selective partition barrier membrane. The barrier membrane can be generally classified as being an ultrafiltration membrane and may be made of ceramic, sintered glass or metal or of a polymeric material such as polyethylene, polypropylene, teflon, cellulose, nylon, etc. and generally has a pore size in the range 100 to 5000Å. The membrane is, preferably, hydrophobic in nature.

The isoparaffin hydrocarbons selectively pass through this porous partition barrier in response to a polar solvent passing, preferably countercurrently, along the opposite face of the barrier membrane. Examples of such polar solvents include aliphatic polyamines such as ethylene diamine, diethylenetriamine or triethylene tetramine, phenol, furfural, acetonitrile sulfolane, N-methyl pyrrolidone, dimethylsulfoxide (DMSO), etc. and mixtures thereof.

In the present process, the feed and extraction solvent can be contacted with the partition barrier at any temperature so long as both the feed and solvent are in the liquid state. Because the separation process is driven by the affinity of the polar solvent for the isoparaffins molecules, the process can be run at atmospheric pressure. Indeed, because of the high porosity of the membrane partition barrier the existence of a pressure differential, either by the direct application of pressure on the feed or solvent side or the creation of a vacuum on either side is undesirable as such a pressure differential would physically force feed or solvent across the barrier and thus defeat its purpose.

EXAMPLES

To illustrate the effectiveness of membranes in iso/-normal paraffin separation, a model compound feed mixture was used (47% 2,2,4-methyl pentane and 53% n-octane). Celgard 2500 which is a micro-porous polypropylene membrane having oval pores of $0.04 \times 0.20$ $\mu m$ used to partition the iso/normal mode compound mixture from DMSO which is a very polar solvent. Since DMSO is very polar, iso-paraffins preferentially permeate to the solvent side.

TABLE

ISO/NORMAL PARAFFIN SEPARATION BY MEMBRANE EXTRACTION

| Stream | Feed | Permeate |
| --- | --- | --- |
| Membrane Extraction | | |
| Membrane | | Celgard 2500 |
| Solvent | | DMSO |
| Temperature, °C. | | 50 |
| Flux, Kg/M2/Day | | 4.1 |
| Composition, % (1) | | |
| Iso-Octane | 47.0 | 61.0 |
| N-Octane | 53.0 | 39.0 |

(1) Determined by GC.

As can be seen from the table, the GC data on the permeate and the feed show that iso/normal paraffin separation was effective by membrane extraction. The feed has 47% iso-octane whereas the permeate has 61% iso-octane. It is important to note that iso/normal paraffin separation cannot be achieved by conventional solvent extraction using a solvent like DMSO. Addition of DMS to the iso/normal octane feed mixture used herein did not yield a significant amount of alkanes in the bottom DMSO phase.

Although only data on iso-octane and n-octane are shown herein, it is expected that the membrane separation described in this specification to be applicable to other iso and normal paraffins. It is also expected that other polar solvents such as acetonitrile and sulfolane would be effective in iso and normal paraffin separations. It is also expected that the separation can be extended to other microporous membranes such as teflon from Gore or nylon from Pall.

What is claimed is:

1. A method for separating isoparaffins from hydrocarbon feeds comprising mixtures of isoparaffins and normal paraffins, said method comprising contacting the hydrocarbon feed in the liquid state with one face of a micro-porous, non-selective partition barrier membrane while simultaneously contacting the opposite face of said micro-porous, non-selective partition barrier membrane with a polar solvent, in the absence of a pressure differential across the membrane, whereby the isoparaffins in the hydrocarbon feed selectively permeate through the micro-porous, non-selective partition barrier membrane in response to the polar solvent on the solvent side of the membrane thereby yielding a permeate enriched in isoparaffins and a retentate of decreased isoparaffin content as compared to the hydrocarbon feed.

2. The method of claim 1 wherein the hydrocarbon feed comprises mixtures of isoparaffins and n-paraffins ranging from $C_4$ hydrocarbon to liquids with final boiling points of about 1050° F.

3. The method of claim 1 wherein the microporous, non-selective partition barrier membrane is an ultrafiltration membrane having pores in the 100 to 5000 Å range 4. The method of claim 3 wherein the ultrafiltration membrane is made of polyethylene, polypropylene, teflon, cellulose or nylon.

5. The method of claim 1, 2, 3, or 4 wherein the polar solvent comprises aliphatic polyamines, phenol furfural, acetonitrile, sulfolane, N-methylpyrrolidone, dimethylsulfoxide and mixtures thereof.

6. The method of claim 1, 2, 3, or 4 wherein the polar solvent is passed countercurrently across the face of the partition barrier membrane as compared to the direction of flow of the hydrocarbon feed passing across the opposite face.

* * * * *